United States Patent [19]

Mueller

[11] Patent Number: 5,797,951

[45] Date of Patent: Aug. 25, 1998

[54] EXPANDABLE SUPPORT MEMBER

[76] Inventor: Edward Gene Mueller, 3840 N. 43rd Ave. #8, Phoenix, Ariz. 85031-2926

[21] Appl. No.: 513,071

[22] Filed: Aug. 9, 1995

[51] Int. Cl.$^6$ ............................................. A61M 29/00
[52] U.S. Cl. ................................... 606/198; 606/191
[58] Field of Search ................................. 606/194, 191, 606/195, 198, 192; 623/1, 12

[56] References Cited

U.S. PATENT DOCUMENTS 5,441,515  8/1995  Khosravi et al. .................. 606/194

*Primary Examiner*—Michael Buiz
*Assistant Examiner*—Kevin Truong
*Attorney, Agent, or Firm*—Gregory J. Nelson

[57] ABSTRACT

An expandable support generally in the form of an annulus. The support has a plurality of segments with sections having cooperating engagement which permit circumferential expansion upon application of force. In a preferred application, the support may be inserted by a balloon catheter into an occluded portion of a blood vessel and expanded to maintain the vessel in an unrestricted condition.

15 Claims, 3 Drawing Sheets

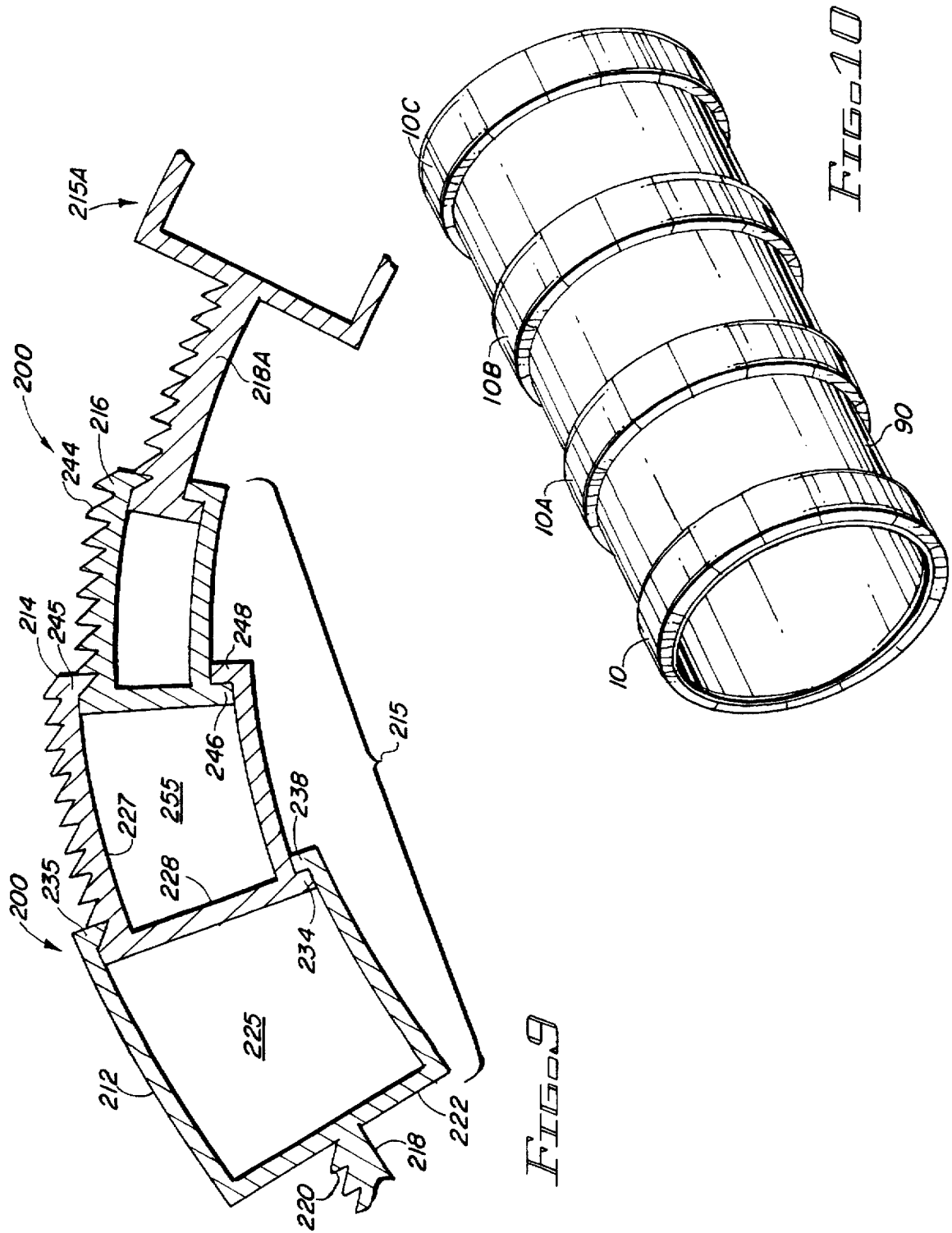

EXPANDABLE SUPPORT MEMBER

BACKGROUND OF THE INVENTION

1. Field of the Invention

This invention is the subject of Document Disclosure filed in the U.S. Patent & Trademark Office on Aug. 16, 1993, No. 337317.

The present invention relates to a support member and more particularly relates to a support member which is expandable to serve as an anchor or a support for both medical and non-medical applications.

Atherosclerosis is a common arterial disorder which is characterized by yellowish plaque formed of cholesterol, lipids and cellular debris on the inner layers of the wall of arterial vessels. The formation of plaque causes the vessel wall to become thick, fibrotic and calcified. As a result, the passageway or lumen within the artery narrows resulting in reduced circulation of blood to organs and areas supplied by the artery. Atheromatous lesions are major causes of coronary heart disease, angina pectoris, myocardial infarction or other cardiac disorders.

There are a number of medical approaches to the problems of this arterial disorder. Segments of arteries obstructed or severely damaged by atheromatous lesions may be replaced by patch grafts or bypassed as in coronary bypass surgery.

One type of surgical procedure that is used to treat this condition is angioplasty. Angioplasty has certain advantages in that it is less traumatic and less invasive than conventional coronary bypass surgery. The patient may be required to remain in the hospital only a short time. In angioplasty surgery, an endoscopic-type probe is inserted into the vessel such as the artery and carefully advanced to the site of the blockage. A balloon located at the end of the catheter is inflated causing the plaque to be dislodged from the interior wall of the artery. The problem with surgery of this type is that the plaque condition will often re-occur within a relatively short time or the artery will constrict causing a reduction in the area of the lumen. In order to maintain the artery in an open position and prevent collapse of the artery at the surgical site, vascular surgeons will often insert a device known as a stent to hold the artery in an open position. Stents are basically tubes which are inserted to prevent the tissue cells surrounding the surgical site from re-closing the affected artery. Stents, while in many cases effective, are surgically difficult to insert and being of fixed diameter cannot be expanded so as to secure them against subsequent dislodgment.

SUMMARY OF THE INVENTION

Briefly, a preferred embodiment of the present invention provides an expandable support constructed of a biomaterial compatible with the human body and which may be deployed by a balloon catheter during angioplasty surgery. The support is comprised of a plurality of segments each having a body section having an interior compartment and a surface which has engagement means. One end of the body section is open to slidingly receive a portion of the next adjacent segment. In a preferred embodiment, the body has a projection which has a plurality of longitudinally extending teeth. In the compressed or retracted position, the projections are fully inserted within the compartment of the body of the next adjacent segment. The segments can be assembled in this way to form a ring-like or annular support construction. When the device is expanded, as by application of radially-applied forces, the annular support will expand as the projections are forced outwardly from their compartments. The plurality of teeth on the projections are similar to ratchet teeth and cooperate with a pawl-like member on the body to secure the support in an expanded position. Expansion beyond the capability of the device is prevented by cooperating stop components associated with each of the members.

The device can be fabricated in a linear form or in an annular form. The device has primary application in conjunction with balloon angioplasty procedures. The device is inserted during the surgical procedure and deployed and expanded by the balloon catheter in the affected area and becomes locked in place after the balloon catheter is removed to maintain the lumen of the artery in an open condition.

The anchor and support device while having a primary application as a medical device can also be used in various other applications such as an annularly or linearly expandable support for use in applications such as an anchor in masonry or concrete structures.

BRIEF DESCRIPTION OF THE DRAWINGS

The above and other objects and advantages of the present invention will become more apparent from the following description, claims and drawings in which:

FIG. 9 is a sectional view of an alternate embodiment of the anchor device of the present invention which provides the advantage of increased expansive length; and FIG. 10 is a perspective view of a plurality of rings in a compressed state joined together by a flexible membrane as a unitary assembly.

DETAILED DESCRIPTION OF THE DRAWINGS

Figure 4:
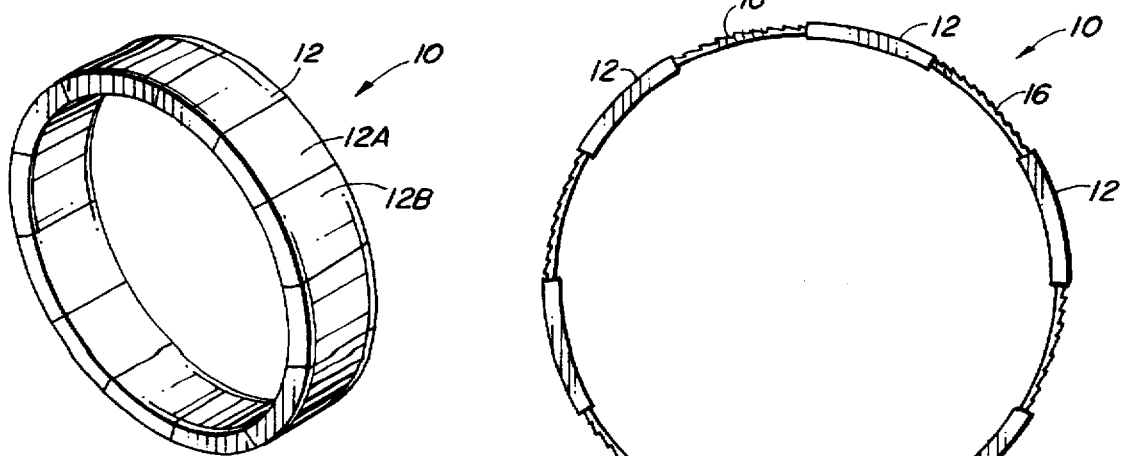
FIG. 4 is a perspective view illustrating an annulus comprised of expandable segments according to the present invention showing the annulus in a compressed condition.
Figure 5:
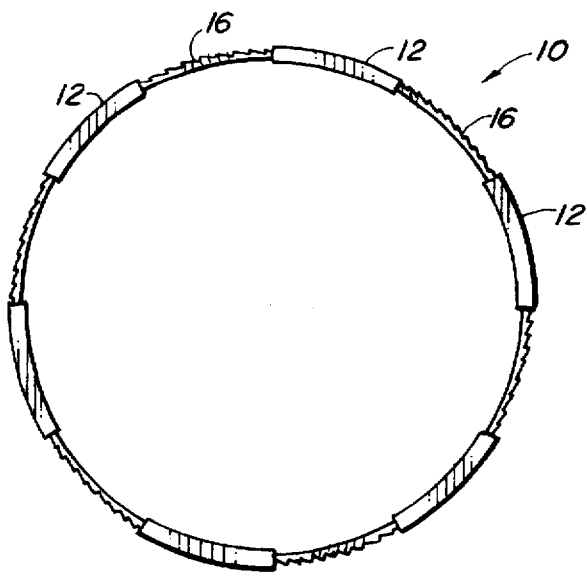
FIG. 5 is an enlarged view similar to FIG. 4 showing the segments in an expanded condition.

Turning now to the drawings, an embodiment of the support of the present invention is generally designated by the numeral 10 and comprises a plurality of individual segments 12, 12A, 12B, etc., which are formed into an annular or ring-like construction. As seen in FIGS. 4 and 5, each of the segments is essentially identical so that a description of one of the segments will be understood to apply to all of the individual segments 12, 12A, etc.

Each segment, as for example segment 12, includes a body member 14 and a projection member 16. The body member 14 has an upper wall 18 and a lower wall 20 and opposite ends 22 and 24. A compartment 25 is defined within the body. Each of the segments is slightly arcuate so that when joined together they will form a ring as described above.

End wall 24 of body member 14 defines an opening 29 between the upper locking member 28 and lower upstanding flange 30 which extends upwardly from the inner surface of the bottom wall 20. Locking member 28 has an inclined surface 32 which defines an acute angle with respect to the end wall 14 and, as will be explained, operates similar to a pawl to lock the projection 16A of adjacent section 12A in an expanded condition.

Figure 3:
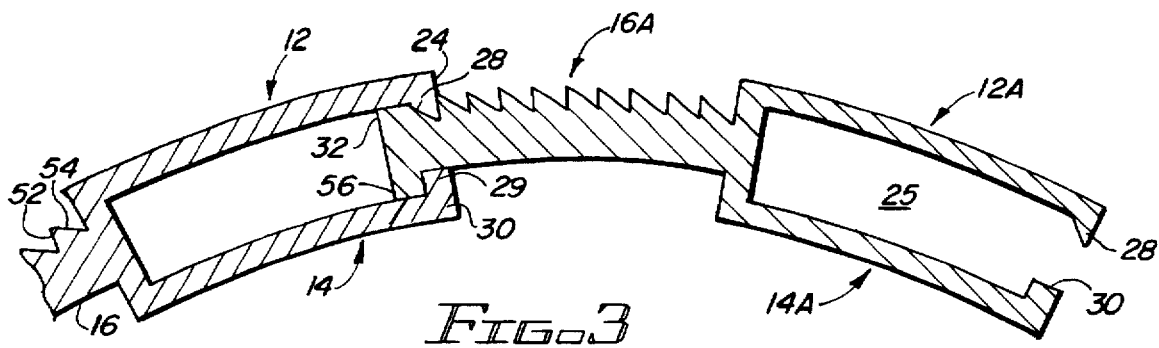
FIG. 3 is a longitudinal cross-sectional view showing the segments in an expanded condition similar to that shown in FIG. 1.

Integrally formed and extending from end wall 22 is projection or slide 16. The projection 16 has a substantially smooth and arcuate bottom surface 42, opposite side walls 44 and 46. The upper surface is provided with cooperating engagement means shown as a plurality of longitudinally spaced-apart teeth 50. Each of the teeth have a profile with a first surface 52 which extends generally vertically and a rearwardly inclined surface 54. The surfaces define a tooth similar in profile to the teeth of a ratchet. The angled surface 54 corresponds generally to the angle of the interior of locking member 28. A downwardly extending stop 56 is provided on the underside of the projection 16 at the distal end as seen in FIG. 3.

Figure 1:
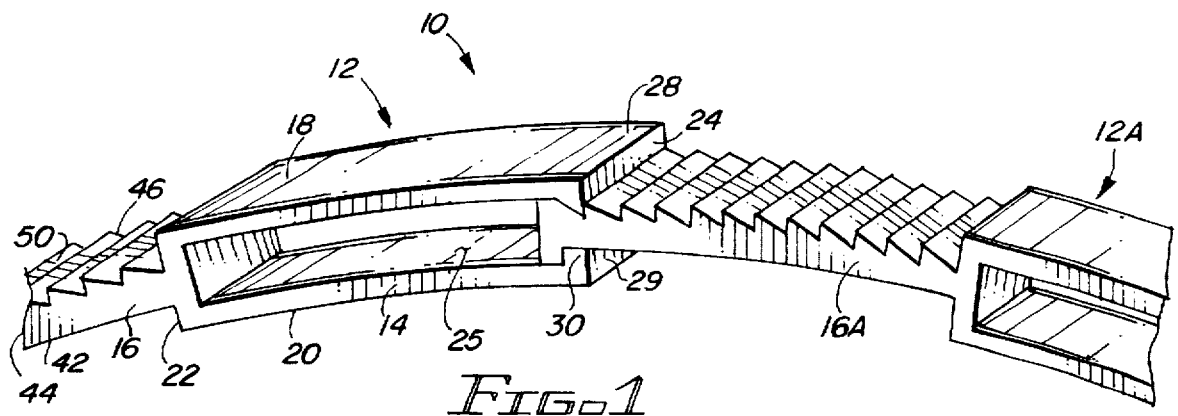
FIG. 1 is a perspective view of a portion of a ring or annulus comprised of a plurality of expandable interlocking segments according to the present invention showing the segments in an expanded condition.
Figure 2:
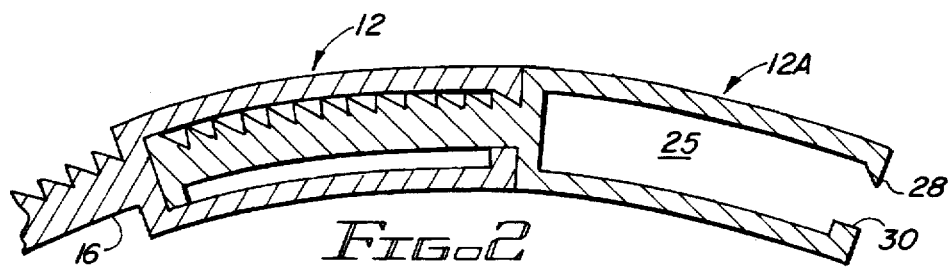
FIG. 2 is a longitudinal cross sectional view through two adjacent segments showing the segments in a retracted position.

A support assembly is formed by interconnecting a plurality of the individual segments 12, 12A, in a retracted position. The assembly, as shown in FIGS. 2 and 4, is in the form of an annulus or a ring. In the retracted position, each of the projection members such as member 16A is fully inserted into the compartment 25 of the next adjacent body member. The assembly can be easily accomplished since compartment 25 of each of the body members is open to facilitate insertion of the projection to the assembled position seen in FIG. 2.

The support 10 of the present invention has particular application in medical procedures, particularly surgical procedures for treatment of atherosclerosis.

Figure 6:
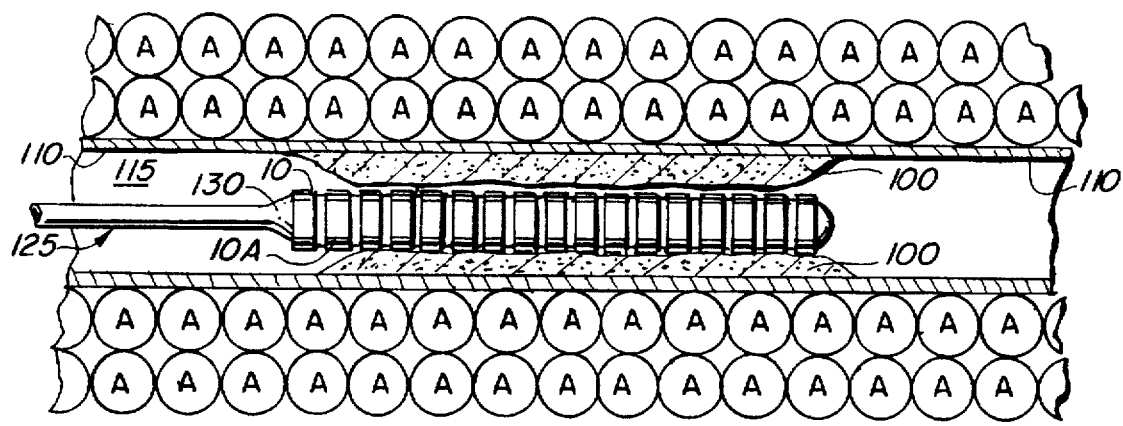
FIG. 6 shows a lateral section of an artery, partially blocked by plaque, in which a balloon catheter has been inserted and on which a plurality of support members in a compressed state have been assembled.

FIG. 6 depicts a lateral section of an affected artery, partially blocked by plaque deposits 100. The vessel, shown as an artery 110, has a lumen 115 which is blocked by the deposits effectively reducing the blood flow and resulting in possible medical complications. As mentioned above, conventional medical procedure is either to bypass the blockage site or to treat the blockage with balloon angioplasty to remove the plaque.

In FIG. 6, a catheter 125 has been inserted into the artery by conventional procedures. The end of the catheter carries an inflatable balloon 130 which is positioned in the occluded section of the artery. A plurality of supports 10, 10A, etc. as described above, have been longitudinally positioned adjacent one another about the exterior of the catheter balloon 130.

Figure 7:
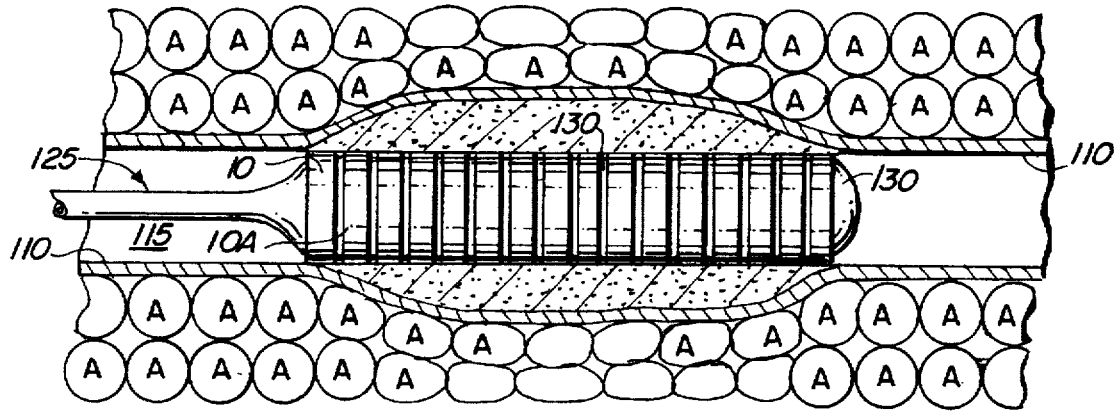
FIG. 7 is a view similar to FIG. 6 and shows a balloon catheter in an inflated configuration within the artery causing the segments to expand outwardly against the plaque deposit and the arterial walls.

In FIG. 7, the balloon 130 has been inflated by conventional methods causing the individual support members to each radially expand. The surrounding cell tissues "A" have been compressed and deformed by the outward and expansive force exerted by the balloon device 130.

Figure 8:
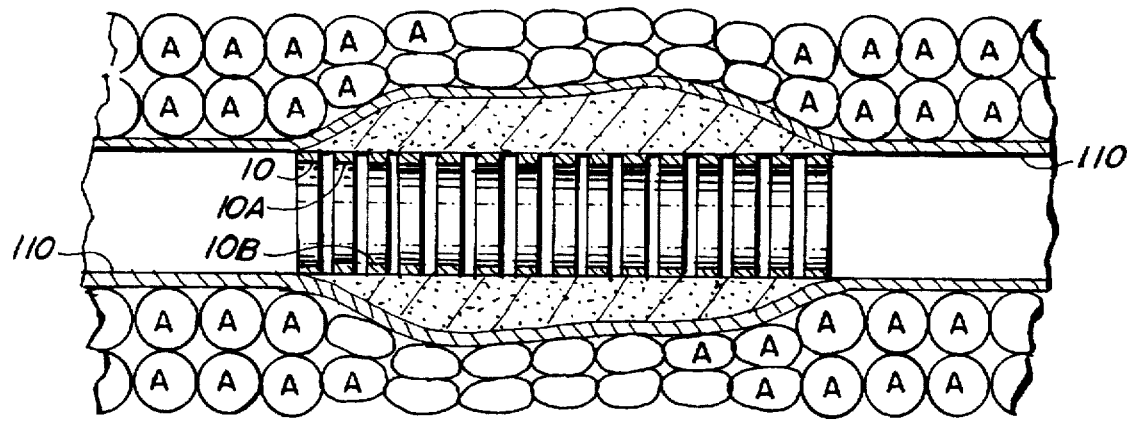
FIG. 8 is a view similar to FIG. 7 showing a plurality of supports according to the present invention locked in place after the balloon catheter has been deflated and withdrawn from the artery.

The medical procedure is completed by deflating by the balloon 130. The catheter and attached balloon are withdrawn from the artery leaving the support member in place, securely deployed against the arterial wall and radial displaced plaque material as seen in FIG. 8. The surrounding cell tissues have also been compressed and will continue to exert pressure attempting to return to the position shown in FIG. 4. The support members, once expanded, will not retract or reduce in diameter. They are held permanently in place, shoring or reinforcing the artery against continued pressure exerted by the deformed cell tissue.

The plurality of teeth 50 permit expansion to any position in which the locking member 28 is in engagement with a selected tooth. FIG. 3 shows full extension of the segments and it is seen that over extension is prevented by engagement of the stop 56 and flange 30. The profile of the ratchet-like teeth allow extension or expansion and engagement with a pawl-like member 24 resists retraction when the device is expanded.

The segments which comprise the support may be made of any suitable material. In medical applications, the material would be a biocompatible material such as a stainless steel or medical grade plastic approved for implantation. Plastics of the type commonly used in implantable heart valves would be suitable for this purpose. The support 10 would be provided to the surgeon suitably packaged in sterile packaging and also provided in different size ranges depending upon the surgical requirements.

FIG. 10 shows an embodiment of the invention in which a plurality of individual support members 10, 10A, 10B and 10C are shown. The individual supports are each constructed as described above with reference to FIGS. 1 through 5. The supports are joined to one another by a flexible membrane or sleeve 90 of biocompatible material. A biocompatible material such as polytetrafluoroethylene works well for this purpose as it is inert and flexible. An assembly consisting of a plurality of interconnected supports may be provided to the surgeon and the surgeon would select the desired length required for the surgical procedure and cut-off the appropriate length of the assembly containing the supports.

In FIG. 9, an alternate embodiment of the invention is shown generally designated by the numeral 200. In this embodiment, a plurality of sections 212, 214, 216 are shown comprising a support segment 215. Section 212 has a body defining interior compartment 225. One end of the chamber is closed at 222 from which extends a projection 218 having teeth 220 formed on one surface of the projection.

Section 214 has a configuration with the bottom wall 226, top wall 227 and end wall 228. Section 214 is in telescopic relationship with member 212. In the retracted or fully collapsed position, section 214 is fully received within compartment 225 of section 212. Top surface 227 of section 214 is provided with engagement means in the form of a plurality of ratchet-like teeth 230 which are cooperatively engageable with pawl-like member 235 on member 212. Similarly, a stop member 238 projects from the inner end of wall 226 and engages a lip 234 on section 235 to prevent disengagement of members 214 and 212 upon extension.

Section 216 is in telescopic relationship with section 214. In the fully compressed position, member 216 is fully received within compartment 235 of section 214. Section 216 has a plurality of ratchet-like teeth 244 on one surface which are engaged by pawl-like member 245 of section 214. A stop consisting of a flange 246 on section 216 and a stop 248 prevents disengagement of section 216 from section 214 upon expansion.

Section 216 has an interior compartment 255 which slidingly receives projection 218A of the next adjacent segment 215A in the assembly.

It will be apparent that an annular support assembly may be formed from a plurality of telescoping segments such as shown in FIG. 10. The annulus may be any desired diameter and size. The advantage of the embodiment shown in FIG. 10 is increased expandability is achieved from the fully retracted diameter of the assembly to the fully extended diameter of the assembly.

While the foregoing has been described with respect to medical applications, it will be appreciated that the support of the present invention has many other applications. For example, an annular support as constructed above, may be used as anchors in masonry construction. In a masonry application, a hole would be drilled and the anchor constructed as described above would be inserted into the hole. An expanding force could be applied by a suitable tool such as a conically-shaped cam inserted into the annulus of the support. The insertion of the cam would apply radial pressure causing the segments to expand and grip the masonry surface.

Also, while the preferred form of the invention is shown with respect to annular or ring-like construction, it will be obvious that the expanding assembly could also be linear for certain applications where non-retractable expandability is required.

While the principles of the invention have been made clear in the illustrative embodiments set forth above, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

I claim:

1. An expandable support assembly comprising:
    (a) a first segment having:
        (i) a first section having a body with opposite first and second walls defining a compartment therein and having an open end communicating with said compartment and further including first engagement means;
        (ii) a second section on said body having second engagement means thereon;
    (b) a second segment having:
        (i) a first section having a body defining a compartment therebetween and having an open end communicating with said compartment and further including first engagement means;
        (ii) a second section on said body having second engagement means thereon;
    (c) said second section of said first segment being received within the compartment of the second segment and being moveable relative thereto to an extended position with the first engagement means of the second segment in engagement with the second engagement means of the first segment.

2. The expandable support assembly of claim 1 wherein said segments are joined to form an annulus.

3. The expandable support assembly of claim 2 wherein a plurality of expandable support assemblies are arranged in side-by-side spaced-apart relationship and are interconnected by a flexible membrane.

4. The expandable support assembly of claim 3 further including stop means associated with one of said segments to limit the extension of said second section relative to said first section.

5. The expandable support assembly of claim 1 wherein said first engagement means comprise a pawl at said open end of said compartment and said second engagement means comprises a plurality of teeth engageable by said pawl.

6. The expandable support assembly of claim 1 wherein said first and second sections are plastic.

7. The expandable support assembly of claim 6 wherein said plastic is a biocompatible material.

8. The expandable support assembly of claim 1 wherein said first wall forms a top side, said second wall forms a bottom side and further including opposite ends and wherein one of said ends defines said open.

9. An expandable support for insertion into a fluid carrying vessel comprising:
    (a) an annular assembly comprised of a plurality of adjacent segments, each segment including:
        (i) a first section having a body with walls defining a generally longitudinally extending compartment, said compartment having a first end and a second end with an opening defined at said first end;
        (ii) first engagement means formed on said body at said first end;
        (iii) a second section having a body, said second section extending from the second end of said body of said first section and having second engagement means thereon, said second section being adapted to be received in a retracted position within the compartment of the first section of the next adjacent segment, said second section being movable relative to said first section of the next adjacent segment from a retracted position to an extended position with said first and second engagement means engaged at selected positions to form an annular assembly of selected diameter and to prevent retraction of said second section from said extended position.

10. The expandable support of claim 9 wherein said first and second sections are comprised of a biocompatible material.

11. The expandable support of claim 9 wherein the body of said second section comprises a projection extending generally axially from said first section.

12. The expandable support of claim 9 further including stop means associated with one of said first and second sections to limit expansion of said support.

13. A medical procedure comprising:
    (a) providing a plurality of segments each segment including:
        (i) a first section of a biocompatible material having a body defining a compartment and having first engagement means associated therewith;
        (ii) a second section having a body of a biocompatible material and having second engagement means associated therewith, said second section being at least partially received in the said compartment of an adjacent segment in a normally retracted position;
    (b) positioning said plurality of segments in an annular arrangement about an expandable delivery device;
    (c) inserting the delivery device and said segments to a predetermined location within a body passageway;
    (d) expanding the delivery device causing said second sections of the segment to be extended relative to the said first sections of the next adjacent segment to a predetermined position whereby said engagement means are engaged to prevent retraction of said second sections bringing said sections into engagement with the passageway to support same; and (e) deflating said delivery device and withdrawing said delivery device leaving said segments location in a supporting position.

14. A component for an expandable support assembly in which the support assembly is comprised of at least two similar adjacently positioned components arranged to form an annulus, said component comprising:

(a) a body having interior and exterior walls and defining an interior compartment, said body defining an opening into said compartment at a first end and having an opposite second end;

(b) pawl means positioned at said first end adjacent said opening;

(c) a projection extending from said second end having a surface with a plurality of longitudinally extending teeth therein; and (d) said projection being received in said compartment of the adjacent component in a retracted position and moveable to an extended position upon application of force and whereby said pawl means engages selected of said teeth to maintain said components in said extended position.

15. The component of claim 14 wherein said interior and exterior walls are substantially smooth.

* * * * *